US005522404A

United States Patent [19]
Williams

[11] Patent Number: 5,522,404
[45] Date of Patent: Jun. 4, 1996

[54] ADJUSTABLE SAFETY AND ASSISTANCE HARNESSING DEVICES

[76] Inventor: Rick Williams, 7102 Ravenswood Way, Boise, Id. 83709

[21] Appl. No.: 319,065

[22] Filed: Oct. 6, 1994

Related U.S. Application Data

[63] Continuation of Ser. No. 995,583, Dec. 22, 1992, abandoned.

[51] Int. Cl.$^6$ .............................. A61F 5/37; A61B 19/00
[52] U.S. Cl. .......................... 128/876; 128/869; 128/875; 297/468; 297/483
[58] Field of Search ........................... 128/869, 874–876, 128/846

[56] References Cited

U.S. PATENT DOCUMENTS

| | | | |
|---|---|---|---|
| 1,316,163 | 9/1919 | Kennedy | 297/485 |
| 2,233,397 | 3/1941 | Bloom | 119/857 |
| 2,877,833 | 3/1959 | Boley | 297/485 |
| 3,046,982 | 7/1962 | Davis | 128/875 |
| 3,276,432 | 10/1966 | Murcott | 128/874 |
| 3,437,089 | 4/1969 | Posey | 128/875 |
| 3,526,432 | 9/1970 | Jensen et al. | 297/483 |
| 3,604,750 | 9/1971 | Doering | 297/389 |
| 3,954,280 | 5/1976 | Roberts et al. | 297/485 X |
| 4,273,215 | 6/1981 | Leggett | 119/857 X |
| 4,289,352 | 9/1981 | Ashworth | 297/473 |
| 4,478,311 | 10/1984 | Anderson | 119/857 X |
| 4,519,106 | 5/1985 | Sandquist | 128/876 X |
| 4,540,218 | 9/1985 | Thomas | 297/464 X |
| 4,632,425 | 12/1986 | Barratt | 280/290 |
| 4,786,078 | 11/1988 | Schreier et al. | 297/483 X |
| 4,807,937 | 2/1989 | Harrigan | 128/874 X |
| 4,827,920 | 5/1989 | Rowell, Sr. | 128/875 |
| 4,879,768 | 11/1989 | McClees et al. | 2/268 |
| 4,919,484 | 4/1990 | Bougher et al. | 297/474 |
| 4,929,027 | 5/1990 | Beauvias, II | 297/482 |
| 4,966,392 | 10/1990 | Featon et al. | 280/801 |
| 4,979,779 | 12/1990 | Williams | 297/465 |
| 4,981,307 | 1/1991 | Walsh | 280/290 |
| 5,026,225 | 6/1991 | McIntyre | 410/23 |
| 5,042,838 | 8/1991 | Carter | 297/483 |
| 5,056,869 | 10/1991 | Morrison | 297/485 |
| 5,088,161 | 2/1992 | Robertson | 297/483 X |
| 5,119,767 | 6/1992 | Jimencz | 280/290 X |
| 5,120,103 | 6/1992 | Kave | 297/473 X |
| 5,154,446 | 10/1992 | Blake | 297/483 X |
| 5,265,910 | 11/1993 | Barr et al. | 297/483 X |
| 5,397,171 | 3/1995 | Leach | 128/875 X |

FOREIGN PATENT DOCUMENTS

| | | | |
|---|---|---|---|
| 0272729 | 9/1964 | Australia | 119/857 |
| 0209258 | 1/1987 | European Pat. Off. | 297/485 |
| 1310485 | 10/1962 | France | 297/465 |
| 1350503 | 12/1963 | France | 128/875 |
| 6935 | 3/1898 | United Kingdom | 280/290 |

*Primary Examiner*—Sam Rimell
*Assistant Examiner*—Brian E. Hanlon
*Attorney, Agent, or Firm*—Wayne E. Duffy

[57] ABSTRACT

The present invention relates to an adjustable safety and assistance harnessing device that is mountable to chairs or wheelchairs. Particularly, there is a harness loop (20) which may be attached to one handle (22) of a wheelchair. Additionally, the harness fits under one arm of a person, across the chest and under the other arm of the person. Moreover, the harness may fit under the other handle (34) and over one shoulder of the occupant where the harness is secured to a slideable clip (30). The clip sliding along the chest portion so as to loosen and tighten the harness system. Therefore, the person is free to bend and move more freely in a loosed harness position, and held more securely in a tightened position.

1 Claim, 2 Drawing Sheets

ADJUSTABLE SAFETY AND ASSISTANCE HARNESSING DEVICES

CROSS-REFERENCE TO RELATED APPLICATIONS

This is a continuation to U.S. patent application Ser. No. 07/995,583, filed Dec. 22, 1992, now abandoned.

FIELD OF THE INVENTION

The present invention relates to wheelchairs and regualr chairs. Particularly, there is a wheelchair that is equipped with a combination safety and motion support or assistance strapping device.

BACKGROUND OF THE INVENTION

Historically

Individuals that are either permanently or temporarily disabled, typically rely on wheelchairs to get from place to place. The need of the wheelchair users are generally no different from those of non users. They must be able to get from place to place in a reasonable time period. They must be physically comfortable or they may tire more rapidly than would otherwise be the case. Furthermore, the individuals who use wheelchairs often have specialized needs. For example, some occupants may require extra devices to hold them in the wheelchair, or they may require a wheelchair with removable arm rests so that they may easily alight or board the wheelchair.

Wheelchairs have been in use for over one hundred years. In recent years, there have been many adaptations made to the original wheelchair. A major source for adaptations has involved devices to allow wheelchair users to become more mobile and self sufficient.

Problems

A major problem with these adaptations have been so designed that prior art harnesses must first be placed about the torso of an individual (which is not always practical to accomplish), and then secured to a chair at the time the individual is placed in the chair. This problem is further compounded whenever the harness is designed with special arm or neck holes, as has been customary for some jackets of the prior art. Also, these holes and openings constrictively encircle or circumscribe the users limbs or neck and are uncomfortable and generally restrict movements. What is even more disturbing is that, as a result of the individual being restricted in his movements by such prior art devices, the possibility for unsafe movement may still be present and may cause additional hazards.

It is noted that the above described problems, as well as other problems, are solved through the subject invention and will become more apparent, to one skilled in the art, from the detailed description of the subject invention.

SUMMARY OF THE INVENTION

One skilled in the art will appreciate the advantage of the subject combination wheelchair or chair and harness device. Specifically, there is an easily adjustable assisting safety harness system using a three or one point of support for a chair or wheelchair. Uniquely, the strapping system has several arrangements, either three or one point of support, allowing for adjustability and a variety of occupant movements.

Other features and objects of the present invention will become more clear from the following detailed description of the invention, taken in conjunction with the accompanying drawings and claims, or may be learned by the practice of the invention.

Figure 1:
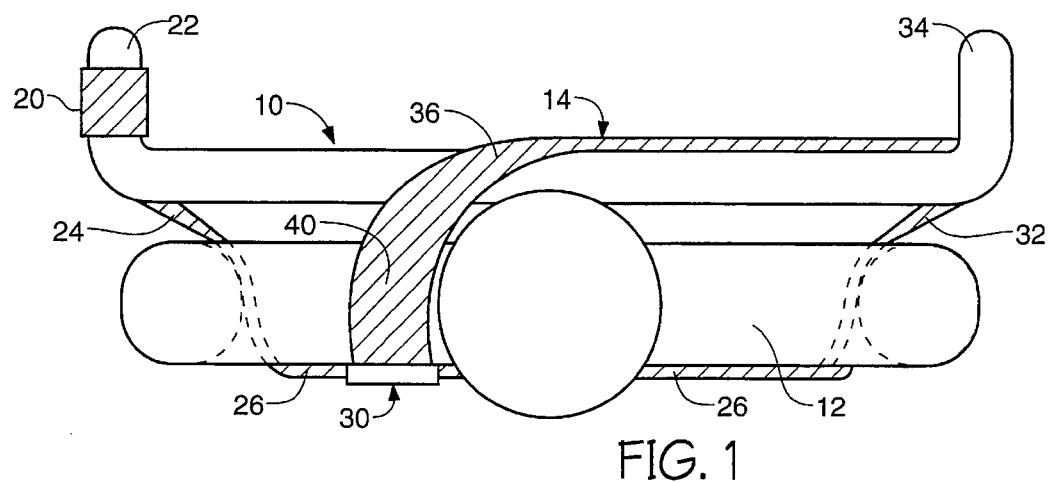
FIG. 1 is a detailed illustration of the invention.

It is noted that the drawings of the invention are not to scale. The drawings are merely schematic representations, not intended to portray specific parameters of the invention. The drawings are intended to depict only typical embodiments of the invention, and are therefore not to be considered limiting of its scope. The invention will be described with additional specificity and detail through the use of the accompanying drawings. Additionally, like numbering in the drawings represent like elements within and between drawings.

DETAILED DESCRIPTION OF THE ILLUSTRATED EMBODIMENT

This disclosure of the invention is submitted in furtherance of the constitutional purposes of the U.S. Patent Laws "to promote the progress of science and useful arts" (Article 1, Section 8 of the U.S. Constitution).

Incorporated Material

The following U.S. patents are herein incorporated by reference for pertinent and supporting information:

U.S. Pat. No. 5,026,225 is a passenger and wheelchair securement system for vehicles. The patent describes an occupant restrain and securement system for vehicles in which a track in two section is disposed in space apart, parallel relationship on the vehicle floor. A frame securement belt is attached to each of the four corners of the wheelchair frame so that four belts secure the chair to the track sections. Independent occupant securement is provided with a lap belt which attaches on each side of the chair to a track section. A shoulder harness attaches to the floor behind the occupant of the chair and rearwardly of the occupant separates into two shoulder sections which have clip loops which secure to the releasable clip of the lap belt. A rear stanchion may be provided by attaching the same to the track sections and passing the rearward part of the shoulder harness over the upper part of the stanchion.

U.S. Pat. No. 4,981,307 is a suspension harness and body jacket arrangement adapted for medical applications. The harness arrangement suspends all or part of the body weight of a patient with respect to a wheelchair's fixed seat, a bed or the floor. The body jacket is seatless, and fabricated from a mesh or fish net material which elongates and grips the patient more snugly depending upon the tension applied thereto by suspension springs. In the case of incapacitated patients confined to the wheelchair, the arrangement may be used to substantially reduce the pressure applied to the patient's buttocks, thus preventing the development of pressure sores.

U.S. Pat. No. 4,979,779 is an apparatus for restraining a portion of the body of an occupant of a wheeled transport vehicle having a seat. The apparatus includes a cloth restraint member and a device for fastening the cloth restraint member around the occupant's body portion. Preferably, the fastening device is centrally located on the front of the cloth restraint member for easy entry and exit of the occupant's body from the cloth restraint member and the wheeled transport vehicle. The apparatus further includes a flexible belt which is interconnected with the seat of the wheeled transport vehicle at each of the belt's ends and which is also interconnected with the cloth restraint member between the belt's ends.

U.S. Pat. No. 4,966,392 is a harness for securing within a vehicle a wheelchair in which an occupant is secured by a lap-belt. The harness being attached not to the chair itself, but to side clips, movable relative to the chair and/or occupant. The buckles being attached to the ends of the lap belt, to anchor straps tending to pull the buckles downwardly and rearwardly. There are holding straps associated with the anchor straps which are connected to forward parts of the buckles via parts of the chair frame. These holding straps are designed to tension the buckles forwardly, in response to decelerating forces applied directly to the chair.

U.S. Pat. No. 3,604,750 is a plurality of harnesses which are taught for converting a chair into a security chair to hold an individual in a sitting position while at the same time permitting comfortable 'shifting movements by the individual. The harnesses are first affixed to a chair and then body holding elements of the harnesses are used to secure a seated individual for safety. The harness for adults includes a seat section, back section and back overlap panel, preferably with an underseat panel interposed between the seat section and back section and a slot along the rear edge of the seat section through which the back section and back overlap panel are drawn after the seat section and under seat panel are stretched about the seat of a chair. Additionally, in the embodiment designed especially for use by adults, the long shoulder straps are preferably fixed at one end to the underseat section, and extended upward behind the back section to locations in the back section from which they are extended to cover the chest of the individual. The adult embodiment has separate thigh straps affixed to the seat section. They are adapted to be drawn separately upwardly between the legs of an individual and over his thighs.

General Embodiment

FIG. 1 is a detailed illustration of the invention and includes the following elements: There is a wheelchair 10, of typical design and variation, occupant 12 is seated upon the wheelchair. Holding strap or harness 14 has several notable positioning and attachment locations. Specifically, loop portion 20, is located at one end of the harness 14, and attaches around the wheelchair's right handle 22. A first harness length 24 is attached to the loop 20 and extends under handle 22 and under the arm of the occupant. A second harness portion 26, extends from the first portion to across the body of the occupant. Attached along the second harness portion 26, is a clip 30. A third harness portion 32, extends from the second portion 26 under the other arm of the occupant and up to and under the left wheelchair handle 34. A fourth harness portion 36, extends from the third harness portion 32, extending up over the back of the wheelchair and thereby over one of the shoulders of the occupant; the drawing illustrates the right shoulder. A fifth harness portion 40, extends from the fourth harness portion, and extends down the front of the occupant and attaches to clip 30.

Figure 2:
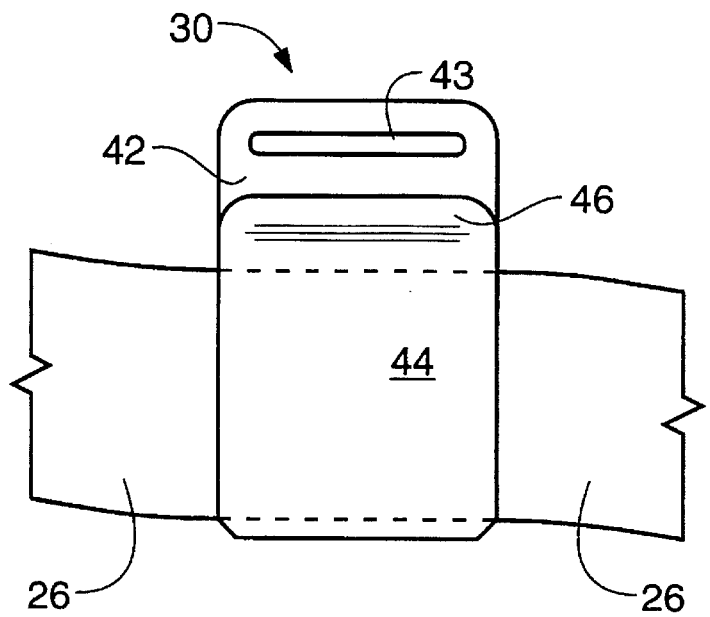
FIG. 2 is a front view of the clip mechanism.
Figure 3:
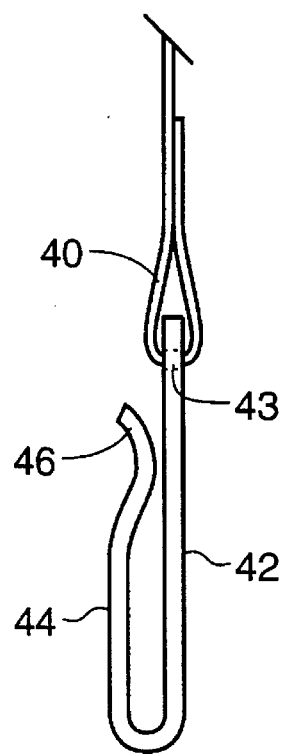
FIG. 3 is a side view of the clip mechanism.

FIG. 2 illustrates a front view and FIG. 3 illustrates a side view of clip 30, these views have the following features: a back plate 42 has a slot 43, a front plate 44, and a lip 46 attached to the front plate. The front and back plates form generally a "U" shape with the ends pinching together for securing the second harness portion 26 which will slidably fit therethrough. Slot 43 serves as an attachment of the fifth harness portion 40 to the clip.

Figure 4:
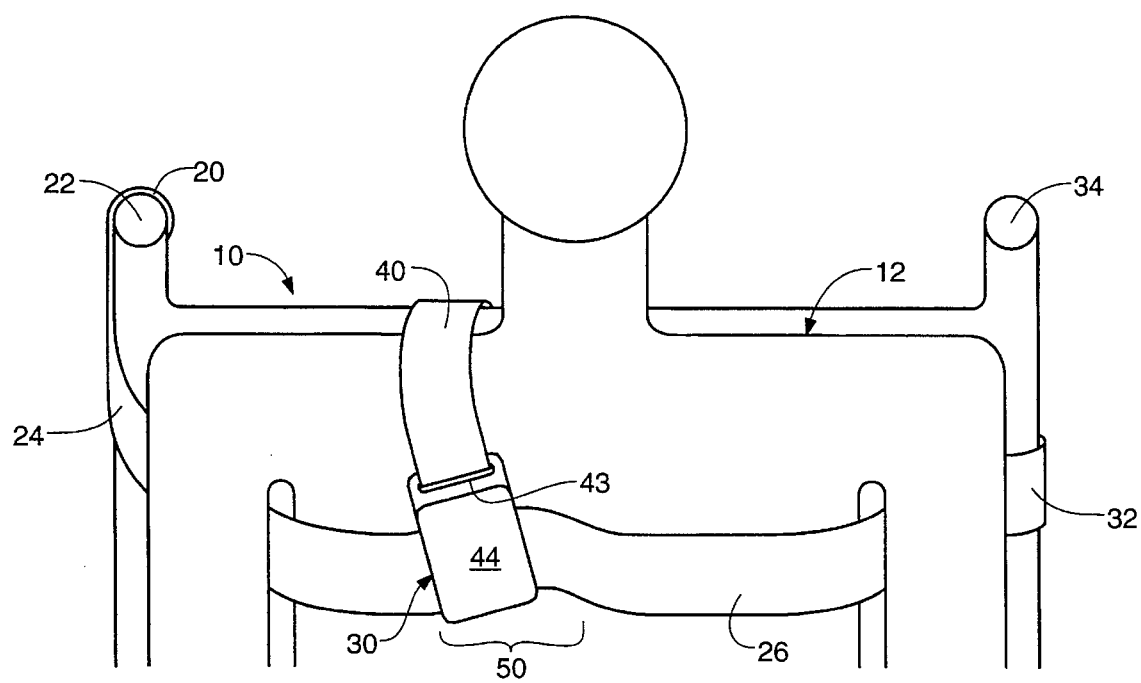
FIG. 4 is a front view of the clip mechanism in use.

FIG. 4 illustrates a front view of the harness system. It is easily understood by anyone skilled in the art of harness systems. Specifically, when a person leans forward, the harness section 40 pulls upward and over the shoulder of the user and crimps the harness section 26 at location 50; roughly coinciding with the harness buckle 30. If the buckle 30 were moved further to the left of the potential occupant, then the tightening created from leaning forward would occur earlier, than if the buckle were moved further to the right. Also, it is easily understood by anyone skilled in buckles and harnesses, that the fact that FIG. 3 illustrates that the buckle is loose at the bottom portion; but is positioned very closely to the back part of the buckle portion 42. In this configuration, anyone with skill in the art will understand that friction of the buckle will add retaining force to the buckle on the safety strap section 26.

Operation of the General Embodiment

Referring to all of the previous figures, the harness system operates as follows: A first operable position is attained by sliding the clip 30 to the right of the occupant the overall tightness of the harness will thereby loosen. In this fashion, the occupant is able to lean forward to a large extent. In a second operable position, clip 30 is slid to the left of the occupant, the harness system tightens, thus securing the occupant much more than the first position.

It is noted that lip 46 provides easy insertion of the second harness portion 26 into the clip.

Variations in the Invention

There are several obvious variations to the broad invention and thus come within the scope of the present invention. Specifically, the harness system will work equally as well whether mounted over the left or right shoulder. Similarly, the overall harness system will work if attached in the opposite fashion, i.e. mounting loop portion 20 on the left wheelchair handle 34.

Uniquely, this invention may work with any form of material in a wide variety of flexible materials. Fabric materials are especially useful. Illustrative fabrics are canvass, duck cloth, quilted cottons, and any other suitable fabric either having sufficient strength to withstand the expected strain during use of the harness or reinforce with straps or strips at high strain areas to impart greater resistance to rupture or tearing. Leather is useful. Plastic film material, optionally reinforced by lamination or quilting to woven or non woven fabric or other sheet material may also be used. Dual layers with intermediate padding or reinforcement may add to the comfort feature of the harness. Stiffeners may be used to impart greater body to different sections such as the back sections of the harness; but generally, at least some drapability is preferably retained in all sections of the harness.

Even possible, and sometimes desirable, is the expedient of forming parts of the harness with elastic material extending completely across its width.

The clip can be up to completly closed at the top portions of the front and back plates; this closure will enable a more secure hold of the harness.

The overall harness system, described above, can be modified by adding two or more portions simultaneously positioned over both shoulders and attaching, with several clips (one for each added harness portion), to the harness portion going across the body.

Additionally, the overall harness system can be modified so that loop 20 has roughly the junction of the third and fourth portions running through it. The loop 20 would not be attached over handel 22 in this case. Thus, the loop would be the pivot point between the third and fourth portions, and be located behind the back of the wheelchair. Also, this arrangement works particularly well for regular chairs. It is noted that this modification can also be used without any chair or wheelchair. In this arrangement, the harness system serves as a second person's means of assisting the harness wearer, ie. for holding onto the person for walking, therapy, or swimming for example.

It is noted, that although the embodiment illustrates a wheelchair, any type of chair, having a seat and back, would also work with the described harness system. In this arrangement, infants and any occupant could be proped up in their chairs.

While the invention has been taught with specific reference to one embodiment, someone skilled in the art will recognize that changes can be made in form and detail without departing from the spirit and the scope of the invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Although subheadings in the Detailed Description of the Illustrated Embodiment are used, these are merely provided for assisting the reader; wherein, the writer is free to enter any information under any heading/s.

What is claimed and desired to be secured by United States Patent is:

1. A combination of an improved harness system and a wheelchair which enables user controlled restraining and positioning and releasing of a seated user of the wheelchair, comprising:

a) a wheelchair having a front and a rear, said rear having a top and a bottom, said wheelchair also having a left side and a right side, each said side having a corresponding handle, each said handle located proximate to the respective right and left shoulders of the seated user, to allow the wheelchair to be controllably moved and guided;

b) a harness system formed from a continuous band of material having first and second ends and having a first attachment means attached to one of said ends and secured about one of said handles for removably and selectively attaching the harness system to said one of said handles of the wheelchair, said harness system further having a second attachment means attached to the other of said ends of the harness system and to a slidable clip means;

c) a first harness portion of the harness system, extending from the first attachment means and the selected handle along a selected one of said sides of said wheelchair to the front of said wheelchair so as to be capable of extending under the proximate arm of the seated user;

d) a second harness portion extending continuously from the first harness portion along the front of said wheelchair to the other of said sides of said wheelchair so as to be capable of extending across the front of the seated user;

e) a third harness portion extending continuously from the second harness portion and along the other of said sides of said wheelchair, up to and under the other of said handles of said wheelchair whereby said third harness portion is capable of extending under the opposing arm of the user in order to controllably limit the forward and lateral movement of the user;

f) a fourth harness portion extending continuously from the third harness portion and the other of said wheelchair handles along the back and over the top of the back of said wheelchair so as to be capable of extending up and over a selected shoulder of the seated user of the wheelchair; and (g) a fifth harness portion extending continuously and downward from the fourth harness portion along the front of the wheelchair toward the second harness portion and being capable of extending down the front of the seated user of the wheelchair, said fifth harness portion terminating at the other of said ends of said harness system, said fifth harness portion being operably and slidably attached to said second harness portion by said second attachment means and said slidable clip means;

(h) said slidable clip means being slidably connected along said second harness portion to controllably position and restrain the user of the harness system in the wheelchair.

\* \* \* \* \*